(12) United States Patent
Balwani et al.

(10) Patent No.: US 6,830,744 B2
(45) Date of Patent: Dec. 14, 2004

(54) COMPOSITIONS METHODS AND SYSTEMS FOR PULMONARY DELIVERY OF RECOMBINANT HUMAN INTERFERON ALPHA-2B

(75) Inventors: Gul Balwani, Fremont, CA (US); Brooks Boyd, Berkeley, CA (US); John Whatley, Hayward, CA (US)

(73) Assignee: Aradigm Corporation, Hayward, CA (US)

( * ) Notice: Subject to any disclaimer, the term of this patent is extended or adjusted under 35 U.S.C. 154(b) by 0 days.

(21) Appl. No.: 10/159,083

(22) Filed: May 31, 2002

(65) Prior Publication Data

US 2003/0223936 A1 Dec. 4, 2003

(51) Int. Cl.[7] ............................ A61K 9/12; A61K 38/21
(52) U.S. Cl. ......................... 424/45; 424/43; 424/85.7; 424/85.4
(58) Field of Search ........................... 424/45, 43, 85.7, 424/85.4

(56) References Cited

U.S. PATENT DOCUMENTS

| | | |
|---|---|---|
| 4,496,537 A | 1/1985 | Kwan |
| 5,509,404 A | 4/1996 | Lloyd et al. |
| 5,522,385 A | 6/1996 | Lloyd et al. |
| 5,558,085 A | 9/1996 | Rubsamen et al. |
| 5,709,202 A | 1/1998 | Lloyd et al. |
| 5,743,250 A | 4/1998 | Gonda et al. |
| 5,766,582 A | 6/1998 | Yuen et al. |
| 5,906,202 A | 5/1999 | Schuster et al. |
| 6,131,570 A | 10/2000 | Schuster et al. |
| 2001/0043906 A1 | 11/2001 | Vlasselaer et al. |

FOREIGN PATENT DOCUMENTS

| | | |
|---|---|---|
| WO | WO 01/49260 A2 | 7/2001 |

*Primary Examiner*—Thurman K. Page
*Assistant Examiner*—Mina Haghighatian
(74) *Attorney, Agent, or Firm*—Karl Bozicevic; Bozicevic, Field & Francis (57) ABSTRACT

Stable aqueous formulations which are free of products derived from human or animal origin and which maintain high biological activity and high chemical and physical stability of alpha-type interferon for an extended period of time. Methods of producing stable aerosol formulations of the same for delivery to the lungs are also provided, as well as systems and methods of delivering the formulations to the lungs for systemic absorption.

34 Claims, 6 Drawing Sheets

Flow Chart of Stability Upon Extrusion & Aerosolization Process Study

Effect of Extrusion & Aerosolization On EP2001 Via SE-HPLC Formulation C

(Bar chart: % Monomer vs Processing Condition)
X-axis labels: C Ctr, C Ctr + UF, C Aero, C Aero + UF, C extr, C extr + UF, C Dimer Ctr, C Dimer + Spike, C Dimer + Spike + UF

FIG. 4A

Effect of Extrusion & Aerosolization On EP2001 Via SE-HPLC Formulation D

(Bar chart: % Monomer vs Processing Condition)
X-axis labels: D Ctr, D Ctr + UF, D Aero, D Aero + UF, D extr, D extr + UF

COMPOSITIONS METHODS AND SYSTEMS FOR PULMONARY DELIVERY OF RECOMBINANT HUMAN INTERFERON ALPHA-2B

FIELD OF THE INVENTION

The present invention relates to stable, aqueous solution formulations of alpha-type interferon for aerosolization and pulmonary delivery thereof.

BACKGROUND OF THE INVENTION

Although recombinant human alpha-type interferon has been available in isolated form for some time, it is currently produced in formulations specifically designed to be administered by injection, e.g., by subcutaneous or intravenous injection. An important perceived advantage of administration by injection is that the dose and activity of the protein can be carefully controlled. For example, the protein can be prepared in stable aqueous form, stored over extended periods without loss of activity or change in its state of aggregation, then administered in a precisely known volume.

U.S. Pat. No. 4,496,537 to Kwan discloses biologically stable alpha interferon aqueous solution formulations containing alpha interferon, human serum albumin and alanine or glycine, water, and a buffer system to maintain the pH at 6.5–8.0. The human serum albumin acts as a stabilizer for alpha interferon and prevents losses of alpha interferon from solution by coating and/or adsorption of the alpha interferon onto the stainless steel and glass surfaces of compounding vessels, process equipment and storage containers. Solution formulations containing alpha interferon and human serum albumin have maintained the chemical and biological stability of the alpha interferon when such solutions have been stored at 2–8° C. for extended periods, i.e., more than 2 years.

U.S. Pat. No. 5,766,582 to Yuen et al. describes a stable aqueous solution of alpha-type interferon that is formulated for subcutaneous injection. U.S. Pat. No. 5,766,582 notes that the worldwide AIDS epidemic has resulted in health registration agencies requiring manufacturers to place warnings on products, such as alpha interferon, which contain products derived from human blood such as HSA (human serum albumin). For this reason, the patent noted the need to reformulate alpha-interferon solution products to obtain a solution formulation free of human blood-derived products such as HSA while maintaining high chemical, high physical stability and high biological activity for alpha interferon in the aqueous solution formulations for extended storage periods.

Subsequent to the filing for U.S. Pat. No. 5,766,582, increased concerns over the spread of spongiform encephalitis have arisen. Because of this, it is now important to formulate compositions containing alpha interferon so as to be free not only of products derived from human blood, but to be free of products derived from animal (such as bovine, for example) origin as well.

Further, there is a need for improved formulations and delivery mechanisms for the delivery of alpha interferon which are more patient friendly and apt to increase patient compliance. Typically, patients show varying degrees of avoidance patterns when it comes to the need to recurrently inject themselves (or have someone else inject them) to administer a drug subcutaneously. This tends to be a factor in non-compliance, with patients often missing some of their scheduled injections which may be forgotten largely due to subconscious avoidance.

By contrast, administering alpha-interferon via an aerosol to the deep lung by inhalation, requires aerosolizing the protein from a concentrated solution of alpha-interferon, which presents several challenges and which the above-noted solutions are not formulated for. In particular, it has not been known heretofore whether and how alpha-interferon could be aerosolized without loss of activity and/or protein aggregation, particularly where the aerosol is formed under shear conditions necessary to produce a desired aerosol-particle size range. Additionally, it has not been known whether or to what degree the protein would pass through the alveolar membranes for systemic delivery. Nor has it been known whether or how alpha-interferon could be formulated at concentrations so that its activity and molecular-size characteristics are maintained over an extended storage condition, yet still allow the desired protein properties and particle-size distribution profile in an aerosol. Nor has it been known the proper formulations, if any, for a therapeutic dose to be systemically delivered via the lungs.

SUMMARY OF THE INVENTION

The present invention provides concentrated stable, aqueous formulations of alpha interferon for aerosol delivery, which are free of human blood-derived products and animal blood-derived products, and which may be efficiently delivered to the lungs of a patient for systemic absorption. The formulations may include about 0.5 to about 12.0 mg alpha interferon per mL of the formulation; a buffer system capable of maintaining the pH of the formulation within the range of about 7.0 to 8.0; a stabilizer; and water.

The preferred alpha interferon is alpha-2b interferon, although the present invention is not limited to use of alpha-2b interferon as other interferons or combinations of one or more other alpha interferons with or without alpha-2b interferon may be employed.

A preferred stabilizer is a poly(oxy-1,2-ethanediyl) derivative, more preferably Polyoxyyethlene 20 sorbitan monolaurate or sorbitan, monododecanoate, also called Polysorbate 20 or Tween 20, most preferably high purity Polysorbate 20 or Tween 20 derived from non-animal sources with low peroxide and low carbonyl content.

The buffer system is preferably Na2HPO4.7H2O and NaH2PO4.2H2O.

One preferred formulation includes about 5.0 to about 6.0 mg alpha-2b interferon per mL of the formulation, about 5.5 to about 6.0 mg Na2HPO4.7H2O per mL[1] of the formulation; about 0.45 to about 0.60 mg NaH2PO4.2H2O per ml of the formulation; about 1.00 to about 2.00 mg Polysorbate 20 per mL of the formulation; and water for injection as the solvent; wherein the amounts of Na2HPO4.7H2O and NaH2PO4.2H2O are adjusted to bring the pH of the formulation to about 7.4 to 7.6.

Further provided is an article of manufacture comprising at least one sterilized component; and a stable, aqueous formulation of alpha interferon for aerosol delivery. The formulation is free of human blood-derived products and animal blood-derived products, and includes about 0.5 to about 12.0 mg alpha interferon per mL of the formulation; a buffer system capable of maintaining the pH of the formulation within the range of about 7.0 to 8.0; a poly(oxy-1,2-ethanediyl) derivative; and water.

The sterilized component(s) of the article of manufacture may include a single dose container which is adapted to be sealed aseptically after receiving the sterile filtered formulation.

A method of providing alpha interferon in a form and concentration able to be systemically delivered to a patient via the lungs is provided, wherein the method includes the steps of: providing an aqueous alpha interferon solution having a known, selected alpha interferon biological activity, and containing a buffering system and a stabilizing agent; packaging a unit dose into the container-closure system and aerosolizing the solution with a device to form an aerosol of aqueous droplets, wherein the aerosol has a fine particle fraction of greater than 50%, preferably about 90 to 100 percent.

The fine particle fraction comprises particles having a mass median aerodynamic diameter of less than about 6.5 microns, preferably less than about 5 microns, more preferably less than about 3.5 microns.

A method to administer alpha interferon to the deep lung of a patient in a form and concentration able to be systemically absorbed and provide a therapeutic dose is provided to include the steps of: providing an aqueous alpha interferon solution being free of human blood-derived products and animal blood-derived products and comprising about 0.5 to about 12.0 mg alpha interferon per ml; a buffer system capable of maintaining the pH of the solution within the range of about 7.0 to 8.0; a sorbitan, monododecanoate; and water; aerosolizing the solution to form an aerosol of aqueous droplets, wherein the aerosol has a fine particle fraction of over 50%, preferably about 90 to 100 percent; and delivering the aqueous droplets to the patient's respiratory tract.

Preferably the alpha interferon is alpha-2b interferon.

These and other objects, advantages, and features of the invention will become apparent to those persons skilled in the art upon reading the details of the formulations, methods and systems as more fully described below.

BRIEF DESCRIPTION OF THE DRAWINGS

FIG. 1 shows the pharmacokinetic concentrations over time of various alpha interferon formulations administered to patients according to the present invention, in comparison with formulations which were subcutaneously injected.

FIG. 2 shows mean concentrations of 2,5 AS over time as patient responses to various alpha interferon formulations administered to patients according to the present invention, in comparison with formulations which were subcutaneously injected.

FIG. 3 is a flow chart describing a study which was conducted to investigate whether or not Polysorbate 20 at varying levels in the formulation can protect the present formulations from forces inherent in the extrusion and aerosolization process.

FIGS. 4A and 4B show SE-HPLC results of the effects of extrusion and aerosolization on formulations according to the present invention.

FIG. 5 shows an exemplary device for carrying out aerosolization methods according to the present invention.

FIG. 6 shows an example of a hand-held AERx System which may be used for carrying out aerosolization methods according to the present invention.

DETAILED DESCRIPTION OF PREFERRED EMBODIMENTS

Before the present formulations, methods and systems are described, it is to be understood that this invention is not limited to particular formulations described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one skilled in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a stabilizer" includes a plurality of such stabilizers and reference to "the nozzle" includes reference to one or more nozzles and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

"Alpha-interferon", as used herein refers to the class of nonglycosylated cytokine proteins of approximately 19.5 kDa having antiviral, immunomodulating, and antiproliferative actions. These can be derived naturally or synthesized by conventional or recombinant DNA technology.

"Recombinant Human Interferon Alpha-2b refers to Human Interferon Alpha-2b that is produced according to the information coded by the alpha-2 sub-species of interferon alpha gene incorporated into the transformed *E coli* host cell by recombinant DNA technology. The lowercase "b" refers to an arginine residue in the twenty-third position of the protein sequence.

"Aerodynamic diameter" is the diameter of a particle with unit density that settles at the same velocity as the particle in question under the influence of gravity.

"Aerosol" means a suspension of particles in a gaseous medium, e.g., air. An "aqueous aerosol" is an aerosol formed from an aqueous solution (i.e., a solution containing water as a solvent).

"Chemical stability" refers to the stability of the drug compound itself. To be chemically stable, the chemical structure remains constant and doesn't degrade.

"Physical stability" refers to the drug staying in solution, as a clear solution. To be physically stable, the drug cannot denature and come out of solution, i.e., the solution stays clear.

"Functional stability" refers to the stability of the formulation when used in an aerosolization device. To have functional stability, good aerosol performance must be achieved consistently. The aerosol generated has the same attributes, e.g., consistent viable fraction throughout.

"Emitted dose" or "ED" is the amount of aerosolized particles of the active ingredient (e.g., recombinant human interferon alpha-2b) that is emitted from a drug delivery device. "Mean emitted dose" is an arithmetic average of the emitted doses released over a repetition of a plurality of deliveries under the same conditions.

"Fine particle fraction" or "FPF" is the fraction of particles in an emitted dose that are of a size capable of reaching the deep lung or alveolar membranes. Unless otherwise indicated, fine particle fraction is calculated herein as that fraction of the particles which are less than or equal to about 3.5 microns as measured by a Cascade Impactor, light scattering methods, phase Doppler particle sizing or other applicable methods.

"Fine particle dose" or "FPD" is the amount of the active ingredient that actually reaches the target zone (i.e., deep lung, alveolar membranes) and is a product of emitted dose and fine particle fraction (i.e., FPD=ED×FPF).

"Microbial Limit Test" or "MLT" refers to the test <61> described in the United States Pharmacopeia to determine the quantity of microorganisms present per mL of the formulation.

"Mass median aerodynamic diameter" or "MMAD" is the aerodynamic diameter of the particle where 50% of the aerosol mass is in larger particles and 50% of the aerosol mass is in smaller particles.

"Particle size distribution" or "PSD" is a description of the way the mass of the aerosol is distributed across the range of aerosol particle sizes.

"Dosage form" or "DF" is a container closure system that is used to hold a dose (or partial dose) of a formulation prior to aerosolizing it.

"Pharmacokinetics" or "PK" refers to the study and characterization of the time course of drug absorption, distribution, metabolism and excretion.

"Pharmacodynamics" or "PD" refers to the study and characterization of the biochemical and physiological response to drugs and their mechanism of action.

"Microbe free" refers to the formulation being rendered free from microorganisms by aseptically passing it through a sterilized microbial retentive filter membrane.

"Subcutaneous injection" is an invasive method of drug delivery in which the drug is injected by a needle beneath the skin. Intramuscular injection or intravenous injection, for example, are other invasive methods of drug delivery utilizing a syringe and a needle for injection.

"System efficiency" is defined as the portion of the drug in the container-closure system that reaches the systemic circulation.

"Bioavailability" refers to the portion of the emitted or delivered or inhaled dose from the container-closure system that reaches the systemic circulation.

"High purity" or "specially purified" are descriptors used herein in reference to stabilizers which are chemically pure, i.e., have a peroxide concentration less than or equal to about 0.5 micro moles per gram and a carbonyl concentration less than or equal to about 1.0 micro moles per gram; and which are biologically pure, i.e., are derived from non-animal sources (e.g., only plant precursors) to eliminate the possibility of animal pathogens.

Formulation

A stable, aqueous formulation of alpha interferon was developed according to the present invention as required for successful systemic delivery of alpha interferon via the deep lung tissues (i.e., alveolar membranes). To be suitable, the formulation needed to be capable of being manufactured and stored in sterile, sealed dosage forms, and exhibit chemical and physical stability over a period of at least six months and preferably 2 years or more at temperatures of about 2 to 5° C. The formulation also had to be capable of withstanding the stresses of aerosolization during the delivery of the drug.

According to one aspect of the invention, it has been discovered that a stable alpha interferon solution containing alpha interferon at a concentration of at least 0.5 mg alpha interferon per mL of solution up to about 12.0 mg/mL; more preferably about 4.0 to about 8.0 mg alpha interferon per mL of solution, even more preferably about 5.0 to 6.0 mg/mL, can be aerosolized into fine particle sizes for delivery to the deep lung with substantially no loss of biological activity and substantially no degradation or denaturation of the alpha interferon compound.

A stabilizing agent is included in the solution to help maintain the alpha interferon in solution. Preferably, the stabilizing agent includes a poly(oxy-1,2-ethanediyl) derivative, such as Polysorbate 20 or Polysorbate 80, more preferably Polysorbate 20 that is low in peroxide and low in its carbonyl content, e.g., high purity Polysorbate 20, available from Sigma Aldrich. The stabilizing agent is preferably present in an amount of about 0.5 to about 2.00 mg per mL of solution. Ethylene diamine tetra acetic acid (EDTA) is preferably not used as a stabilizing agent as it has been shown in some studies to cause bronchospasms and was therefor considered to be unsuitable to the present formulations as presenting too high a risk factor for aerosol delivery of the formulations to the lung.

A buffering system is added to the solution to adjust it to a pH of about 7.0 to 8.0, more preferably within the range of about 7.4 to 7.6. A preferable buffering system includes about 5.5 to about 6.0 mg Na2HPO4.7H2O per ml of solution and about 0.45 to about 0.60 mg NaH2PO4.2H2O per mL of solution The solvent is water which is preferably microbe free, free of particulate matter, and free of chemical contaminants, preferably water for injection.

Therapeutic proteins must be formulated so that they are able to withstand a variety of conditions in the course of manufacture, shipping, storage and use. Screening studies were conducted to see whether or not increasing stabilizer levels could potentially improve the stability of aqueous solutions containing alpha interferon during long-term storage in various container-closure systems. The screening studies included subjecting bulk formulations to mechanical shear, thermal cycling, and aerosolization, such as via the AERx® pulmonary delivery system available from Aradigm Corporation, Hayward, Calif. The bulk formulations were assessed for chemical and physical stability under various processing conditions:

As a result of the testing, it was determined that the solutions should contain at least about 0.5 mg Polysorbate 20, preferably about 1.0 to about 2.0 mg Polysorbate 20 per ml of solution for protection during thawing and processing (e.g., filtration, filling dosage forms, freeze/thaw cycling, short term storage at around 2° to 8° C., preferably about 5° C.). Tween 20R (by Sigma Aldrich), a specially purified, non-animal, low peroxide, low carbonyl surfactant is the preferred stabilizer. The bulk formulations containing stabilizer are preferably kept frozen at about −70° C., and are thawed at about 2 to 8° C., preferably about 5° C., for at least 12 hours. Solutions having other stabilizers were tested including solutions with 0.5 mg/mL Polysorbate 20; solutions with 130 mM sodium chloride and EDTA; solutions with 0.1 mg/mL Polysorbate 20; and solutions with 0.1 mg/mL Polysorbate 20 and 130 mM sodium chloride.

Aerosolization

The present inventors have discovered that an alpha interferon solution formulated as above can be aerosolized under conditions that produce particles in a selected size range of less than about 5 microns, more preferably less than about 3.5 microns, with little or no loss in biological activity of the alpha interferon and little or no change in the chemical activity of the alpha interferon.

The aerosol may be produced by any of a number of devices designed to produce particles in the stated ranges from liquid formulations preferably by forcing the formulation, through pores in a membrane wherein the liquid is driven by hydrostatic pressure, preheating the air into which the aerosol is generated, and subsequently delivering the aerosol to a patient. However, it will be obvious to those skilled in the art that many other methods of aerosol generation can be used, or where various other drivers such as piezoelectric oscillators, jet nebulization, ultrasonic nebulization, spinning top aerosolization, magneto-hydrodynamic (electrospray) aerosolization, or ultrasonic vibration of a porous membrane are employed to generate the aerosol. Examples of applicable aerosolization devices are described in U.S. Pat. Nos. 5,509,404; 5,522,385; 5,558,085; 5,709,202; 5,743,250; 5,906,202 and 6,131,570, each of which is incorporated herein, in its entirety, by reference thereto. Preferably, the AERx® pulmonary delivery system available from Aradigm Corporation, Hayward, Calif. is used for aerosol generation according to the present invention. The size of the nozzle holes is in the range of 0.25–6 micrometers or preferably 0.4–3 micro meters, more preferably 0.5–1.5 micrometers. The amount of liquid aerosolized, per inhalation, is in the range of 10–100 microliters, preferably 25–50 microliters, more preferably 35–45 microliters.

Figure 5:
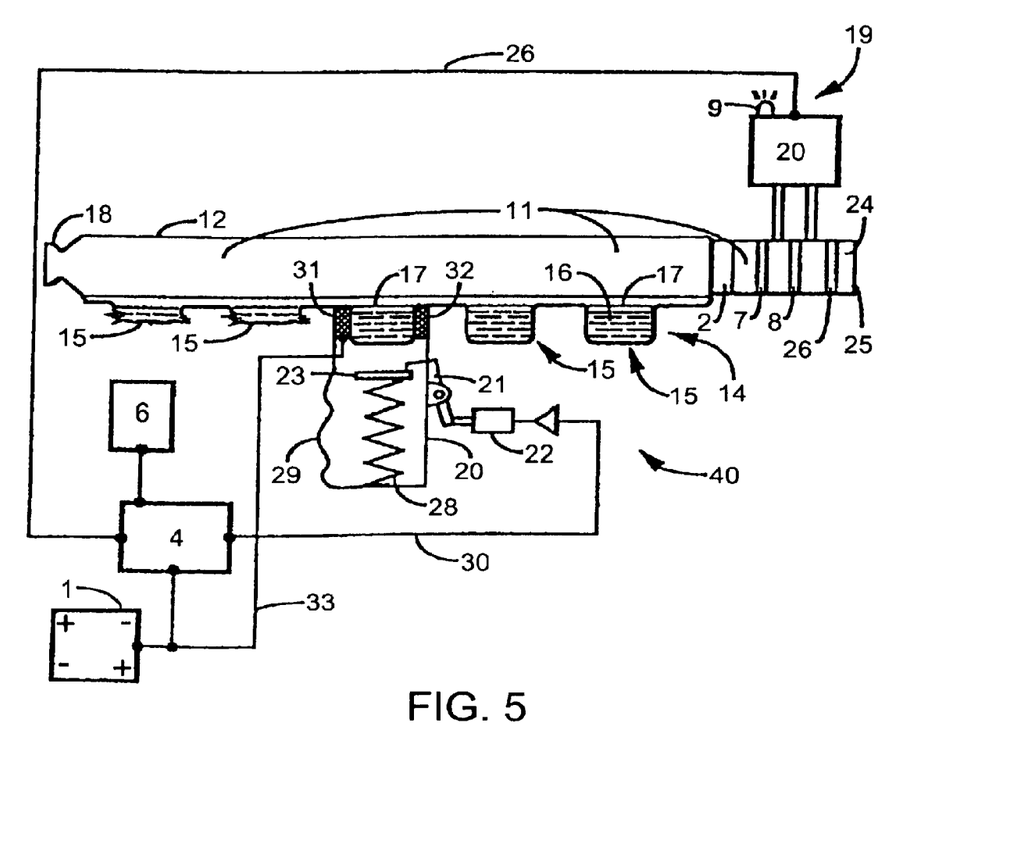

FIG. 5 shows an exemplary device for carrying out the aerosolization methods according to the present invention and is described in detail in U.S. Pat. No. 6,131,570. The device 40 is loaded with a disposable package 14. To use the device 40, a patient inhales air from the mouthpiece 18 through the opening 25 in the cylinder 12. The air drawn in through the opening 25 (and optionally the desiccator 24) flows through the flow path 11 of the channel 12. The disposable package 14 is comprised of a plurality of disposable containers (or "blister packs") 15. Each container 15 includes a drug formulation 16 (i.e., an alpha interferon formulation according to the present invention) and is covered by a nozzle array or porous membrane 17. The heating element 2 (which is optional for methods according to the present invention) is located in the flow path 11. The heating element 2 is preferably positioned such that all or only a portion of the air flowing through the path 11 will pass by the heating element 2, e.g., flow vent flaps can direct any desired portion of air past the heating element 2.

The device 40 may include a mouth piece 18 at the end of the flow path 11. The patient inhales from the mouth piece 18 which causes an inspiratory flow to be measured by flow sensor 19 within the flow path which path may be, and preferably is, in a non-linear flow-pressure relationship. This inspiratory flow causes an air flow transducer 20 to generate a signal. This signal is conveyed to a microprocessor 4 which is able to convert the signal from the transducer 20 in the inspiratory flow path 11 to a flow rate in liters per minute. The microprocessor 4 can further integrate this continuous air flow rate signal into a representation of cumulative inspiratory volume.

When the device is turned on by the user, the microprocessor 4 will send a signal to send power from the power source 1 (which is preferably a small battery) to the air temperature controller 2 and will continue to preheat the temperature controller 2 until it reaches a predetermined temperature. The preheat temperature can be preprogrammed based on such information as the particle size generated, the particle size desired, the formulation concentration, and other parameters. The microprocessor 4 may also adjust the preheat temperature to optimize each delivery based on the ambient conditions, using information from the optional hygrometer/temperature sensor 7. The microprocessor 4 also sends a signal to an actuator 22 which causes the mechanical means (e.g., the piston 23 to force drug from a container 15 of the package 14 into the inspiratory flow path 11 of the device 40 where the aerosol is formed and entrained into the inhalation air and delivered into the patient's lungs.

Since the formulations according to the present invention include water as the carrier, it may also be desirable to include a desiccator 24 within the flow path 11. The desiccator 24 is preferably located at the initial opening 25 but may be located elsewhere in the flow path 11 prior to a point in the flow path when the formulation is fired into the flow path in the form of aerosol particles. By drawing air through the desiccator 24 water vapor within the air is removed in part or completely. Therefore, only dried air is drawn into the remainder of a flow path. Since the air is completely dried, water carrier within the aerosol particles will more readily evaporate. This decreases the energy needs with respect to the temperature controller 2.

When a patient (not shown) inhales through the mouth piece 18 air flows in through the opening 25 and is sensed by the air flow sensor 26 after being electronically converted by the transducer 20. The signal flows along the electrical connection 26 to the microprocessor 4. The combination of the control circuit 6 and the microprocessor 4 send a signal back through the connection 26 to the heating element 2 which is powered by the battery 1. The amount of power to be supplied to the heating element 2 is also tempered, to a degree, by information received from the humidity sensor 7 and temperature sensor 8 which information is considered by the microprocessor 4. When the heating element 2 reaches the correct temperature and the air flow sensor 26 determines that the inspiratory flow rate and inspiratory volume are at the desired point the microprocessor 4 sends a signal to the actuator 22. The actuator 22 may be any type of device such as a solenoid, which then moves the mechanical release member 21 so that the piston 23 is released. The piston 23 is forced upward by a spring or other biasing means 28. The biasing means may be held within a grip 29 which can be easily held by the user. Where the microprocessor 4 sends the signal through the line 30 to the actuator 22 the spring is released and a container 15 is crushed and the formulation 16 inside the container is released through the membrane 17.

When the container 15 is present in the drug release position below the piston 23 the container 15 may have vibrating devices 31 and 32 positioned on either side or a single device surrounding the container 15. The vibrating device(s) may be actuated by the microprocessor 4 sending a signal through the connection 23. Empty containers 15 are shown to the left of the drug actuation point. Preferably, a new container and new porous membrane are used for each drug release. By using a new porous membrane each time clogging of the porous membranes is avoided. Further, possible contamination of the formulation 16 present in the container 15 is avoided.

Those skilled in the art will recognize that a variety of different components could be used in place of some of the components shown within FIG. 5. For example, rather than including a piston biased by a spring it would be possible to utilize a rotating cam. Further, other components of the invention, although preferred, are not required. For example, components such as the humidity sensor 7 and temperature sensor 8 could be eliminated without substantial impairment of operability by simply adjusting the amount of energy supplied to the heating element 2 so as to compensate for any humidity or temperature which might be encounter by the user. However, such would acquire the use of unnecessary amounts of power in some situations.

Dosage Forms

Although liquid formulations according to the present invention can be packaged in various dosage forms of various size and volume, the preferred dosage forms 15 are of a "blister pack" type design 15 which have a volume of about 50 microliters. The packs or containers 15 are filled with about 45±2.5 microliters of alpha interferon formulation. They are not completely filled to provide a space between the formulation and the lid of the pack 15 as it is heat sealed to enclose the package. The space prevents denaturation of the proteins in the formulation which might otherwise occur if in contact with the lid or top of the package as it is heated during heat sealing.

Performance of Aerosolized Delivery of Alpha-Interferon

Formulations were developed for a dose escalation study to compare the safety, pharmacokinetics and pharmacodynamics of the systemic performance of alpha-interferon delivered through the lungs with that of subcutaneously injected Intron® A (Schering Corporation, Kenilworth, N.J.). A therapeutic dose of Intron® A is about 3 million units of the interferon given three times a week for the treatment of Hepatitis C. Based on this value, a formulation for aerosol delivery was back calculated. The aerosolization of the formula was optimized to maximize the amount of fine particle fraction (less than 5 microns, more preferably less than about 3.5 microns) to ensure delivery to the deep lungs in an efficient manner. Given this optimization, it was determined that about 60% of the contents of the blister container is aerosolized as the emitted dose, when the container is compressed by the delivery device. The fine particle dose, or dose that actually reaches the deep lung and alveolar membranes was determined to be at least about 54% of the contents of the blister container. The bioavailability of the drug was estimated to be about 10% of the dose delivered to the lung. Given that the blister container was to contain about 45 microliters of the formulation, a formulation containing 250 micrograms (65 million units @2.6×10⁸ units/mg) was used to deliver a therapeutic dose equivalent to the subcutaneous injection of Introng® A. The formulation that was used for the test comparisons is indicated in Table 1 below where amounts per dosage form as well as amounts per mL are tabulated.

TABLE 1

Formulation Composition

| Component | Amount per DF | Amount per ml |
|---|---|---|
| RH INF a-2b, EP | 0.2500 mg | 5.56 mg |
| Na2 HPO4.7 H2O, USP | 0.2613 mg | 5.81 mg |
| NaH2PO4.2 H2O, USP | 0.0234 mg | 0.52 mg |
| Polysorbate 20, NF | 0.0450 mg | 1.00 mg |
| WFI, USP | q.s. ad 45 µL | q.s. ad 1.0 ml |

* Actual quantity weighed depends on the chemical assay
Final pH adjusted to 7.5 using 25 mM solution of Na2 HPO4/NaH2PO4
Fill volume = 45 ± 2.25 µL (±5%)

The Intron® A formulations that were used in the comparison were prepared from lyophilized product in vials. Each vial contained 5 MIU of Interferon alfa-2b to be reconstituted with 1 mL of the diluent. After reconstitution with the diluent, each mL of the formula contained 0.019 mg or 5 MIU of interferon alfa-2b, 20 mg of glycine, 2.3 mg sodium phosphate dibasic, 0.55 mg of sodium phosphate monobasic, and 1 mg of human albumin. Two vials were used in the clinic to deliver the 10 MIU dose subcutaneously. In conducting the comparisons, a partial dose (only a portion of one container) a full dose and a double dose of the formulation according to the present invention were administered, as well a subcutaneous dose of Introng® A equivalent to 10 million units of alpha-2b interferon. The 10 million unit dose was necessary to obtain measurable PK parameters for comparison purposes. Table 2 shows the contents, emitted doses and lung doses of the partial, single and double extrusions of formulations which were aerosolized.

TABLE 2

Label Claim: 250 µg/DF

| DF's | Extrusion | Contents (µg) | Contents (MIU) | Emitted Dose (µg) | Emitted Dose (MIU) | FPD (Lung Dose) (µg) | FPD (Lung Dose) (MIU) |
|---|---|---|---|---|---|---|---|
| 1 | Partial | 250 | 65 | 47 | 12.2 | 45.6 | 11.9 |
| 1 | Full | 50 | 65 | 150 | 39 | 145.5 | 37.8 |
| 1 | Full | 500 | 130 | 300 | 78 | 291.0 | 75.7 |

65 MIU/DF is based on specific activity of 2.6 × 10⁸ IU/mg

Fifteen subjects were treated with subcutaneous injections of Introng® A, two received the partial dose (partial extrusion) of aerosolized alpha interferon, 3 subjects received the single extrusion (one full dosage form) and 8 subjects were treated with two aerosolized dosage forms (two full dosage forms). The safety results showed 41 adverse events with the patients treated by subcutaneous injection (33 mild, 8 moderate) and 22 adverse events (all mild) regarding the patients treated by aerosolized delivery. Six of the moderate events were "flu-like" symptoms and two were hypotension.

Figure 1:
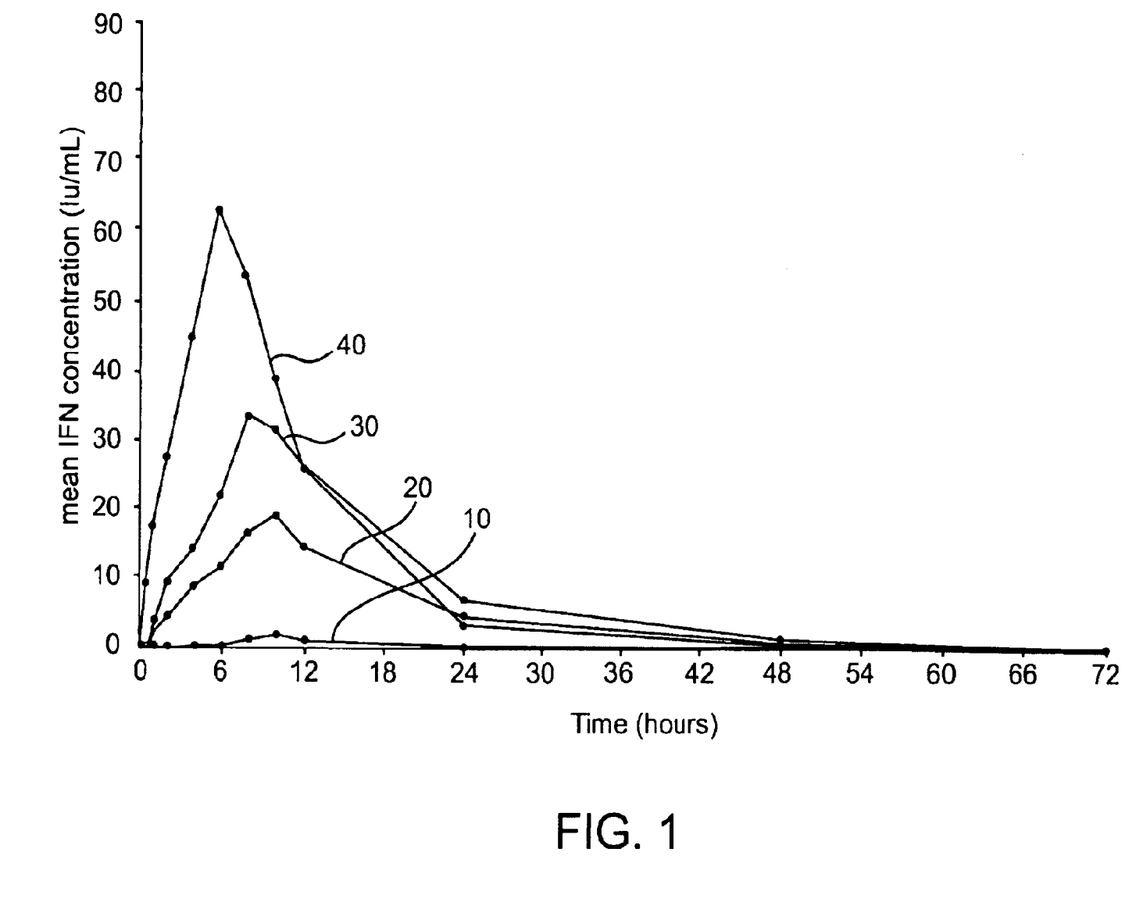

FIG. 1 shows the pharmacokinetic results of the various treatments wherein systemic drug concentrations were determined by serum analysis. Concentrations of interferon (IU/mL) are graphed over time (Hrs) for a period of 72 hours. As was expected, the concentration of alpha-interferon delivered by subcutaneous injection 40 gave the highest spike at about 6 hours, with the double dosage form delivery 30, single dosage form 20 and partial dosage form 10 registering peaks only slightly later and in proportionate concentrations. The concentration for each type of administration tapered off substantially by about 24 hours.

Figure 2:
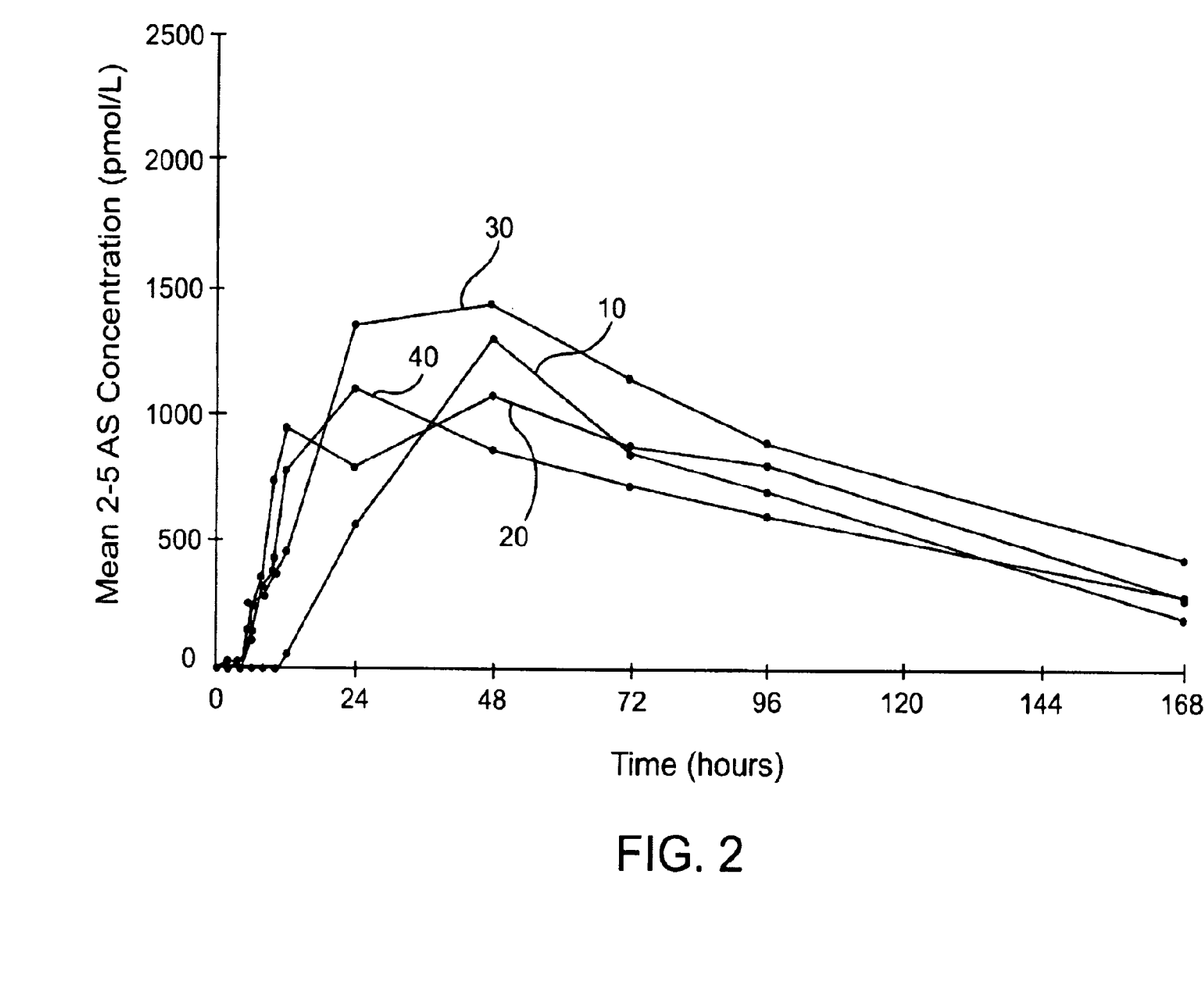

The pharmacodynamics of each type of administration of the alpha-interferon was measured according to the blood concentration of 2'–5'-oligoadenylate synthetase (2–5 AS) and analyzed by standard techniques. Mean concentrations for subcutaneous 40, double dosage form aerosol 30, single dosage form aerosol 20 and partial dosage form aerosol 10 are plotted with respect to time in FIG. 2. The 2–5 AS marker is a traditionally accepted standard for measuring the pharmacodynamics of interferon alpha activity. These results show that, pharmacodynamically speaking, there is not a direct, linear relationship between the concentration of alpha-interferon administered by injection, and varying concentrations of alpha-interferon delivered through the lungs. More specifically, it is noted that the aerodynamic administration of the double dosage form 30 gives a greater 2–5 AS profile than even the subcutaneous injection 40. Even a partial dose 10 elicits a 2–5 AS response level greater than that of the subcutaneous injection 40 at a period of about 48 hours after administration.

Although the present inventors are not certain of the reasons behind the increased pharmacodynamic responses of the aerosolized deliveries relative to subcutaneous injection, these characteristics can provide certain advantages over subcutaneous delivery of alpha-interferon. For example, a much smaller dose can be given by aerosol to a patient on a daily basis, with expectation of achieving the same pharmacodynamic response as if a much larger dose was given subcutaneously or intravenously every three days, which is currently the practice. With daily inhalation, there would be no drop off of the pharmacodynamic response, as it can be seen in FIG. 2, that concentrations of 2–5 AS do not begin to taper generally until after about 48 hours.

For treatment of hepatitis C, the current therapy is to subcutaneously inject about 3 million units of alpha interferon, three times a week. This routine can be met by aerosol delivery of 1 blister dosage form, three times a week, to give a therapeutic dose that is non-invasive. However, since the pharmacodynamic properties are not discriminating based on the dose, a lower dose may be given. As noted, it may be of value to maintain a sustained level by daily dosage (people don't want to inject daily, but inhalation daily may be easier to maintain compliance). Although the pharmacodynamic response lasts long enough that injections of three times a week are possible, it may further be advantageous to give aerosol administration every day, since this is more routine and patients may be less likely to forget to dose. This also may be advantageous to provide a steady antiviral state allowing the body to clear the virus much more quickly and efficiently. Injections of alpha interferon are currently also likely to cause local irritation at the site of the injection. This side effect has not been reported with aerosol administration of the drug.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Stability of Formulation During Freezing

Bulk solution of human recombinant alpha-2b interferon was obtained in a frozen state (under dry ice) and was stored at about −70° C. until processing. The bulk was thawed at 5° C. and filtered through a filter membrane (e.g., a membrane having 0.22 micron pores) prior to further processing. It was observed that the bulk solutions supplied were both chemically and physically unstable upon thawing. In order to provide a robust aqueous formulation of alpha interferon having sufficiently high concentrations of alpha interferon to provide a therapeutic dose via inhalation into the lungs, the formulation had to also be made to be physically, chemically and functionally stable, as well as microbe free with endotoxin levels less than threshold level established as safe, i.e., less than 500 IU/mL Since bulk solutions are shipped frozen, it is paramount that they be stable to the freeze/thaw process. Accordingly, a process study was executed to investigate what role freezing rates and formulation variables had on bulk stability, and to obtain information on the robustness of the bulk solution to exaggerated processing conditions related to manufacture (i.e., mechanical shear and multiple freeze/thaw cycling). Table 3 lists the compositions of three formulated bulk solutions that were subjected to different freezing rate algorithms and subsequent exaggerated processing conditions.

TABLE 3

Composition of Bulk Solutions of Interferon Alpha-2b

| Solution Description | Composition | Method of Freezing Bulk |
|---|---|---|
| A | 5.7 mg/mL Interferon Alpha-2b, 25 mM phosphate, pH 7.5 | Slow freezing at −70° C. |
| B | 6.2 mg/mL Interferon Alpha-2b, 25 mM phosphate, 130 mM NaCL, 0.3 mM EDTA, pH 7.5 | Slow freezing at −70° C. |
| C | 5.9 mg/mL Interferon Alpha-2b, 25 mM phosphate, 0.1 mg/mL Tween 20, pH 7.5 | Slow freezing at −70° C. |
| A | 5.7 mg/mL Interferon Alpha-2b, 25 mM phosphate, pH 7.5 | Rapid freezing with liquid nitrogen |
| B | 6.2 mg/mL Interferon Alpha-2b, 25 mM phosphate, 130 mM NaCL, 0.3 mM EDTA, pH 7.5 | Rapid freezing with liquid nitrogen |
| C | 5.9 mg/mL Interferon Alpha-2b, 25 mM phosphate, 0.1 mg/mL Tween 20, pH 7.5 | Rapid freezing with liquid nitrogen |

Both rapid and slow freezing rate algorithms were employed. Flash freezing of bulk solutions with liquid nitrogen simulated a rapid freezing algorithm. Placing bulk solutions at −70° C. simulated a slow freezing algorithm. All bulk solutions were slowly thawed (5° C.) and a portion was filtered through a 0.22 μm membrane. Post-filtered bulk solutions were subjected to the following simulated processing conditions: (1) 48 hours of constant shaking (500 rpm) at 25° C., and (2) 5-freeze/thaw cycles (slow freezing at −70° C. and thawing at 5° C.). The processed bulk solutions (both pre and post filtered) were assessed for any chemical or physical instability by the following methods: visual inspection with a fiber light, light scatter at 450 nm, RP-HPLC, and reduced and non-reduced SDS-PAGE. Based on the findings of these studies a method for freezing the bulk solution and selection of an appropriate formulation matrix that provided maximum solution stability for alpha-2b interferon was recommended.

Table 4 lists the results for pre and post filtered bulk solutions.

TABLE 4

Physical & Chemical Analysis of Interferon Alpha-2b Bulk Solution Following Thawing at 5° C.

| Solution ID | Method of freezing | Visual Inspection | Light Scatter on pre filtered Solution (absorbance units, AU | Light Scatter on post filtered Solution (absorbance units, AU | RP-HPLC on pre filtered Solution (% LS*) | RP-HPLC on post filtered Solution (% LS*) |
|---|---|---|---|---|---|---|
| A | Slow | Suspended particulars | 0.77 | 0 | 99.3 | 98.6 |
| B | Slow | Suspended particulars | 4.0 | 0 | 92.4 | 19.0 |

TABLE 4-continued Physical & Chemical Analysis of Interferon Alpha-2b
Bulk Solution Following Thawing at 5° C.

| Solution ID | Method of freezing | Visual Inspection | Light Scatter on pre filtered Solution (absorbance units, AU | Light Scatter on post filtered Solution (absorbance units, AU | RP-HPLC on pre filtered Solution (% LS*) | RP-HPLC on post filtered Solution (% LS*) |
|---|---|---|---|---|---|---|
| C | Slow | No Particulates | 0 | 0 | 104.2 | 101.4 |
| A | Rapid | Suspended particulars | 0.01 | 0 | 101.0 | 75.8 |
| B | Rapid | No Particulates | 0.02 | 0 | 98.5 | 97.1 |
| C | Rapid | String/fibril Particulates | 0.05 | 0 | 96.3 | 96.3 |

The visual & light scatter results show that bulk solutions A & B encountered significant particle formation during the slow freezing process. Bulk solution C formed no visible particulates, and no light scatter following a slow freeze algorithm. Only bulk solution B encountered a significant drop in protein content following filtration. This suggests protein loss was most likely attributed to insoluble aggregates that were removed during filtration. It should be noted that the initial protein content of pre-filtered bulk solution B was well below the intended target label claim (~6.2 mg/mL). The pre-filtered bulk solution B encountered no apparent loss in protein content when rapidly frozen.

Pre-filtered bulk solutions A and C that were subjected to the rapid freeze algorithm contained visible particulates with a concomitant slight light scatter. No visible particulates were found in pre-filtered bulk solution B. However, a slight light scatter was observed. RP-HPLC analysis showed significant protein loss only in post-filtered bulk solution A. Post-filtered bulk solution B & C showed no protein loss when subjected to the rapid freeze/thaw algorithm. The results indicate that bulk solution co-formulated formulated with EDTA and sodium chloride in phosphate buffer is more stable when subjected to a rapid freezing rate. Bulk solution containing phosphate buffer alone is more stable with a slow freezing rate.

Example 2

Long Term Stability Monitoring

The following two clinical formulations were selected for long term stability monitoring:

(1) Formulation C: 5.7 mg/mL Interferon-alpha-2b, 25 mM sodium phosphate, 0.5 mg/mL Polysorbate 20 (w/v), pH 7.5

(2) Formulation D: 5.7 mg/mL Interferon-alpha-2b, 25 mM sodium phosphate, 1.0 mg/mL Polysorbate 20 (w/v), pH 7.5

The formulations were aseptically filled (45 μL) in dosage forms 15 and stored at 5° C., 25° C./40% RH, & 40° C. for up to 6 months (product at 40° C. was only monitor for 1 month). The formulations were also filled (1 mL) in sterile polypropylene screw cap vials and stored at 5° C. and RT as controls. The stability samples from the vials and dosage forms were assessed for chemical and physical stability, and functionality (only for dosage forms) using the following methods: RP-HPLC, SE-HPLC, reduced & non-reduced SDS-PAGE, IEF, and pH At the 2-month time pull the two clinical formulations were compared to determine which was most stable. Only the formulation demonstrating the greatest stability was continued on stability monitoring. At the end of the 6-month stability monitor program a minimum shelf life was proposed based on the combined data set.

The chemical and physical stability of the two clinical formulations C and D stored in polypropylene vials at 5° C. and 25° C./40% RH was compared to the commercial liquid product Introng® A. Due to a limited supply of Intron A only 0.5 mL was aseptically filled in sterile polypropylene vials with screw cap. The product was stored at 5° C. and RT for up to 6 months. The commercial product was assessed for chemical and physical stability using the methods listed above (no functional test was conducted since product was not filled into dosage forms 15). The results for the comparisons of the formulation in the polypropylene containers are shown in Table 5 and the results for the comparisons between formulations C and D in the dosage forms are shown in Table 6.

TABLE 5

Comparison of Chemical Stability (RP-HPLC) of Intron ® A with Formulations C & D when Stored in Polypropylene Containers

| Solution Description | % Component Present By RP-HPLC | | | |
|---|---|---|---|---|
| | Sulfoxidized | Oxidized | Post Oxidized | Other |
| Intron A, t = 0 | 2.79 | 94.18 | 1.45 | 1.59 |
| Intron A, t = 1 mo at 5° C. | 2.93 | 93.82 | 1.55 | 1.70 |
| Intron A, t = 1 mo at 25° C. | 4.74 | 87.46 | 2.53 | 5.27 |
| Intron A, t = 2 mo at 5° C. | 3.25 | 95.37 | 1.38 | — |
| Intron A, t = 2 mo at 25° C. | 8.10 | 83.89 | 3.43 | 3.92 |
| Intron A, t = 6 mo at 5° C. | 4.30 | 81.25 | 2.41 | 12.05 |
| Form C, t = 0 | 2.80 | 95.06 | 1.15 | 0.87 |
| Form C, t = 1 mo at 5° C. | 3.25 | 92.47 | 2.98 | 1.30 |
| Form C, t = 1 mo at 25° C. | 3.40 | 90.20 | 3.86 | 2.53 |
| Form C, t = 2 mo at 5° C. | 3.44 | 93.77 | 1.16 | 1.64 |
| Form C, t = 2 mo at 25° C. | 3.57 | 92.42 | 1.10 | 2.90 |
| Form C, t = 6 mo at 5° C. | 2.49 | 93.83 | 3.14 | 0.54 |
| Form C, t = 6 mo at 25° C. | ND | 69.05 | 10.58 | 20.37 |
| Form D, t = 0 | 2.46 | 93.46 | 2.73 | 1.27 |
| Form D, t = 1 mo at 5° C. | 3.32 | 93.17 | 2.08 | 1.42 |

TABLE 5-continued

Comparison of Chemical Stability (RP-HPLC) of Intron ®
A with Formulations C & D when Stored in Polypropylene Containers

| Solution Description | % Component Present By RP-HPLC | | | |
|---|---|---|---|---|
| | Sulfoxidized | Oxidized | Post Oxidized | Other |
| Form D, t = 1 mo at 25° C. | 3.53 | 91.73 | 2.73 | 1.27 |
| Form D, t = 2 mo at 5° C. | 3.47 | 94.96 | 1.57 | — |
| Form D, t = 2 mo at 25° C. | 3.81 | 94.34 | 1.85 | — |
| Form D, t = 6 mo at 5° C. | 2.63 | 92.64 | 1.83 | 2.90 |
| Form D, t = 6 mo at 25° C. | 3.09 | 73.14 | 2.89 | 20.88 |

ND = None detected
— = Not determined

TABLE 6

Comparison of Chemical Stability (RP-HPLC) of
Formulations C & D when Stored in Dosage Form

| Solution Description | % Component Present By RP-HPLC | | | |
|---|---|---|---|---|
| | Sulfoxidized | Oxidized | Post Oxidized | Other |
| Form C, t = 0 | 2.80 | 95.06 | 1.15 | 0.87 |
| Form C, t = 1 mo at 5° C. | 3.56 | 94.67 | 1.34 | 0.18 |
| Form C, t = 1 mo at 25° C. | 3.40 | 93.56 | 2.51 | 0.27 |
| Form C, t = 2 mo at 5° C. | 2.60 | 94.11 | 1.67 | 1.51 |
| Form C, t = 2 mo at 25° C. | 2.85 | 88.51 | 3.93 | 4.51 |
| Form D, t = 0 | 2.46 | 93.46 | 2.73 | 1.27 |
| Form D, t = 1 mo at 5° C. | 2.23 | 96.56 | 0.92 | 0.19 |
| Form D, t = 1 mo at 25° C. | 2.53 | 95.31 | 1.47 | 0.52 |
| Form D, t = 2 mo at 5° C. | 2.51 | 93.61 | 2.27 | 1.61 |
| Form D, t = 2 mo at 25° C. | 2.93 | 88.67 | 3.53 | 4.78 |
| Form D, t = 6 mo at 5° C.* | 2.81 | 95.12 | 2.07 | Trace levels |

*Re-assayed at t = 7.5 mo

Example 3

Effects of Aerosolization and Extrusion on
Chemical and Physical Properties

Figure 3:
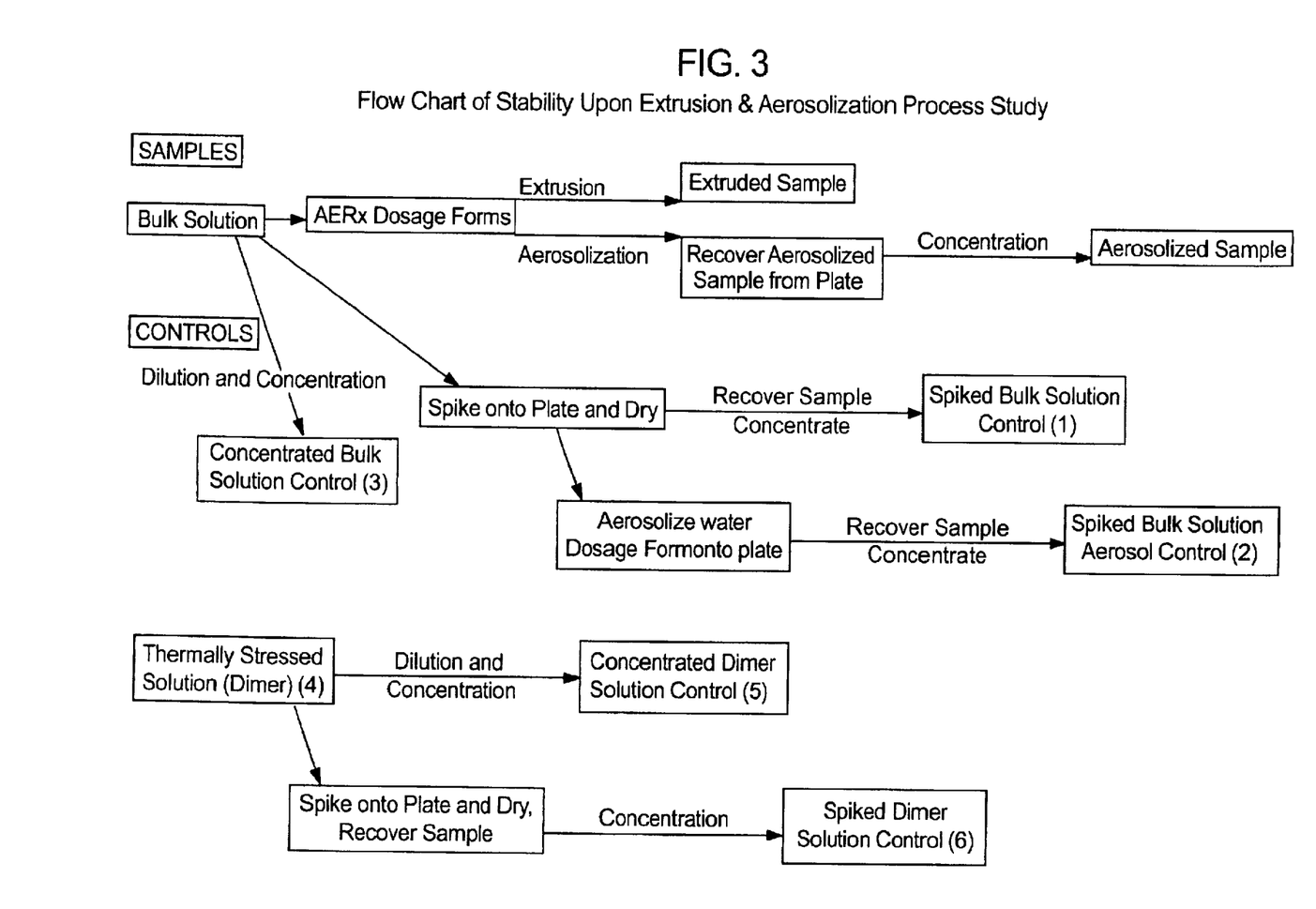
Figure 6:
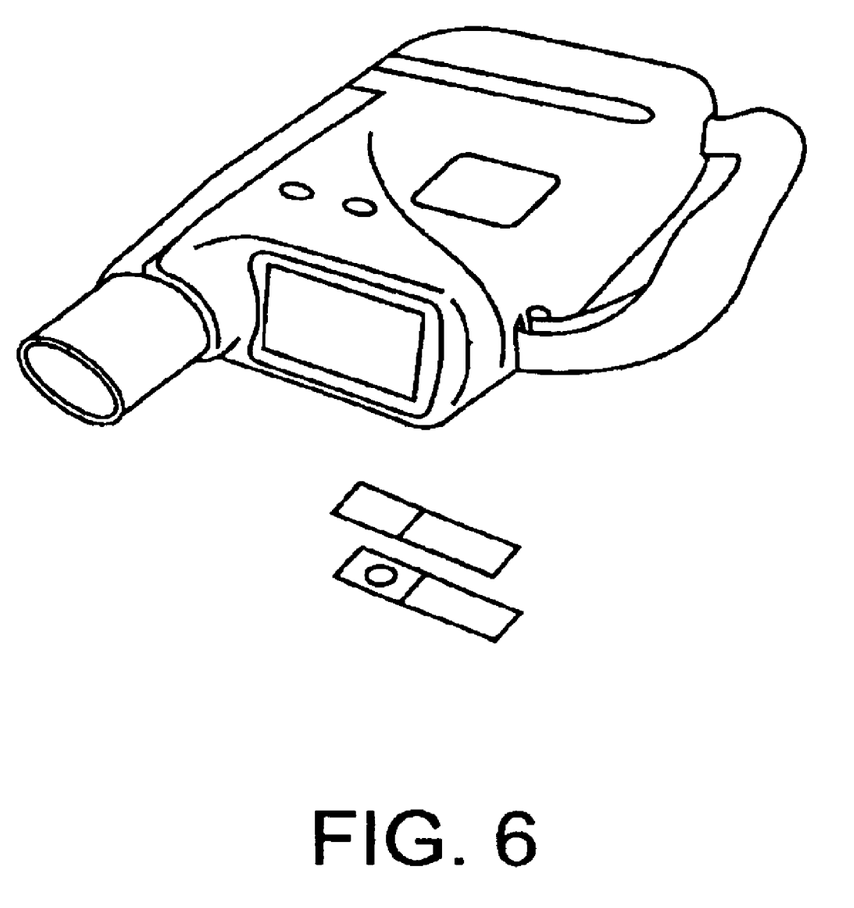

Aerosolization results in subjecting the formulation to shear, exposure to air/water interfaces and drying. There were concerns that these effects may adversely impact the conformational structure of the alpha interferon and consequently its bioactivity. Bioassay testing showed that bulk formulations according to the present invention and Intron® A had a comparable biological potency (both antiviral and immune modulating activity). A study (a schematic flow chart of the study is shown in FIG. 3) was executed to investigate whether or not Polysorbate 20 at varying levels in the formulation can protect the present formulation from effects inherent in the aerosolization process. Formulations C and D were filled (45 µL) in dosage forms 15 and utilized to produce the processed samples. Both reference (Formulation C & D used to fill dosage forms) and degraded solutions (Formulation C incubated at 40° C. for 1 month containing ~2–3% dimer) were used as controls formulation were found under pressure, through a nozzle array of approximately 1 micrometer nozzle holes, and collected (n=10 dosage forms were required). Aerosolized samples (n=2 dosage forms) were generated using the AERx System, an example of which is shown in FIG. 6. The aerosolized samples were collected using a shortened Anderson Cascade Impactor (CI). The pooled aerosolized samples (~40 µg/mL after dilution) were concentrated ~8 fold by ultrafiltration (used Millipore Centricon YM-3) to a target concentration of ~300 µg/mL.

As a control to aerosolization experiment both reference and degraded solutions were spiked (~200 µg/mL) onto the CI plates and allowed to dry. The dried protein was recovered using diluent. The controls were concentrated via ultrafiltration to a target concentration of ~300 µg/mL. A control to the ultrafiltration process entailed diluting both active and degraded solutions from ~200 µg/mL to ~40 µg/mL with diluent and then concentrating to a target protein content of ~300 µg/mL.

All processed samples and controls were tested using the following analysis: SE-HPLC, non-reduced and reduced SDS-PAGE, and IEF.

Figure 4A:
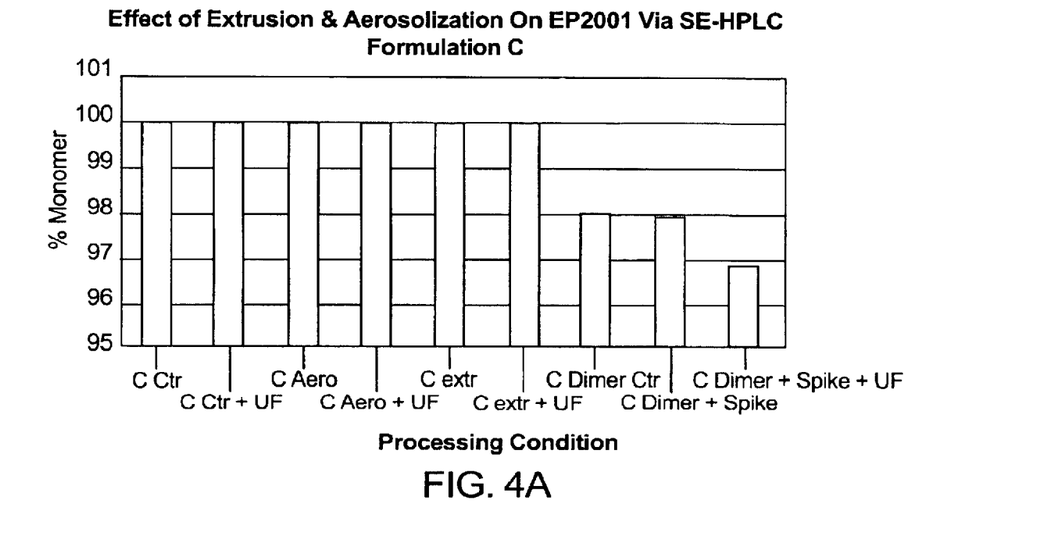
Figure 4B:
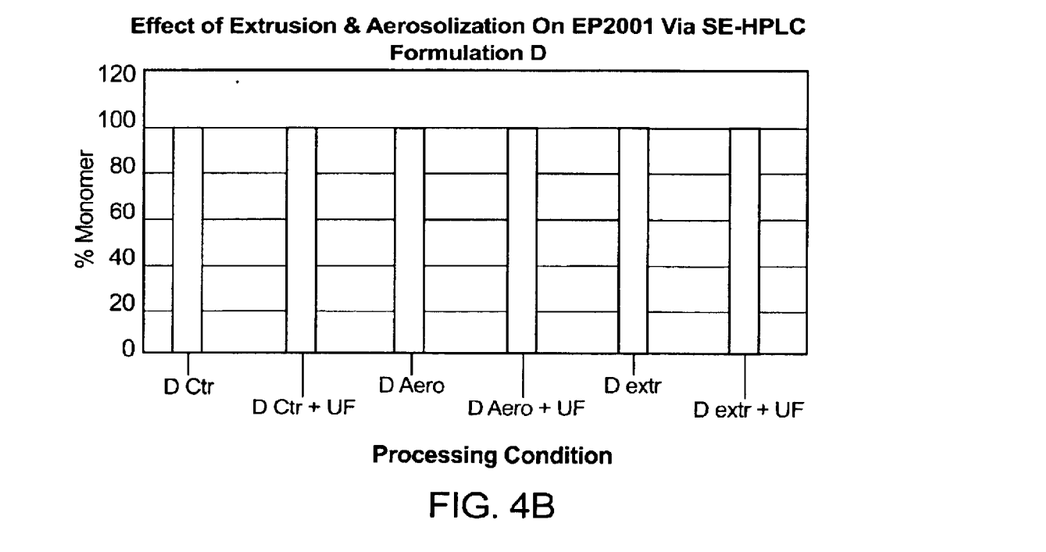

The effects of extrusion and aerosolization on the formulations are shown in FIGS. 4A and 4B. The SE-HPLC results showed that no dimer was formed in either Formulations C or D after extrusion and aerosolization. The controls showed that the ultrafiltration process did not damage the formulations. The results demonstrated that the SE-HPLC method was stability indicating with regards to detection of dimer and fragments formed in the product. Recovery of dimer from processing equipment surfaces (spiked onto the CI plates and ultrafiltration unit) demonstrated that the protein was not changed or lost due to adsorption during sample generation and processing.

With regard to the SDS-PAGE (non-reduced and reduced) and IEF profiles of the formulations, no low or high molecular weight species were formed in either Formulations C or D following extrusion and aerosolization. The SDS-PAGE method had adequate sensitivity to detect low and high molecular weight species in thermally stressed formulation C. No changes in the isoelectric point of the formulations, or formation of charged species was apparent in any of the formulations that were extruded or aerosolized. The IEF method was able to detect acidic species in thermally stressed formulation C. The SE-HPLC and gel data demonstrated that formulations containing both 0.5 mg/mL and 1.0 mg/mL Polysorbate 20 provided protection from shear, surface effects, short exposure to mild temperature conditions, and partial drying inherent to the aerosolization process.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. An aerosolized stable, aqueous formulation of alpha interferon for aerosol delivery, said formulation being free of human blood-derived products and animal blood-derived products, said formulation comprising:
   about 4.0 to about 12.0 mg alpha interferon per mL of the formulation;

about 5.5 to about 6.0 mg $Na_2HPO_4.7H_2O$ per mL of the formulation;

about 0.45 to about 0.60 mg $NaH_2PO_4.2H_2O$ per mL of the formulation;

at least about 0.5 mg Polysorbate 20 per mL of the formulation; and water for injection as the solvent; wherein the amounts of $Na_2HPO_4.7H_2O$ and $NaH_2PO_4.2H_2O$ are adjusted to bring the pH of the formulation to about 7.0 to 8.0.

2. The formulation of claim 1, wherein said alpha interferon comprises alpha-2b interferon.

3. The formulation of claim 1, wherein said alpha interferon consists of alpha-2b interferon.

4. The formulation of claim 1, wherein the concentration of alpha interferon is about 4.0 to 8.0 mg per mL of solution.

5. The formulation of claim 4, wherein the concentration of alpha interferon is about 5.0 to 6.0 mg per mL of solution.

6. The formulation of claim 5, wherein the concentration of alpha interferon is about 5.56 mg per mL of solution.

7. The formulation of claim 1, wherein the concentration of Polysorbate 20 is about 1.0 to about 2.0 mg/mL of the formulation.

8. The formulation of claim 1, wherein the concentration of alpha interferon is about 5.0 to about 6.0 mg per mL of the formulation, the concentration of Polysorbate 20 is about 1.00 to about 1.50 mg per mL of the formulation, and the amounts of $Na_2HPO_4.7H_2O$ and $NaH_2PO_4.2H_2O$ are adjusted to bring the pH of the formulation to about 7.4 to 7.6.

9. The formulation of claim 8, wherein said alpha interferon comprises alpha-2b interferon.

10. An aerosolized stable, aqueous formulation of alpha interferon for aerosol delivery, said formulation being free of human blood-derived products animal blood-derived products, said formulation comprising:

about 4.0 to about 12.0 mg alpha interferon per mL of the formulation;

a buffer system capable of maintaining the pH of the formulation within the range of about 7.0 to 8.0;

a poly(oxy-1,2-ethanediyl) derivative; and water.

11. The formulation of claim 10, wherein said buffer system comprises about 5.5 to about 6.0 mg $Na_2HPO_4.7H_2O$ per mL of the formulation and about 0.45 to about 0.60 mg $NaH_2PO_4.2H_2O$ per mL of the formulation.

12. The formulation of claim 10, wherein said poly(oxy-1,2-ethanediyl) derivative comprises Polysorbate 20.

13. The formulation of claim 12, wherein said Polysorbate 20 is added at a concentration of at least about 0.5 mg per mL of the formulation.

14. The formulation of claim 13, wherein said Polysorbate 20 is added at a concentration of about 1.0 to about 2.0 mg per mL of the formulation.

15. An aerosolized stable, aqueous formulation of alpha interferon for aerosol delivery, said formulation being free of human blood-derived products and animal blood-derived products, said formulation comprising:

about 5.5 to about 5.6 mg alpha-2b interferon per mL of the formulation;

about 5.5 to about 6.0 mg $Na_2HPO_4.7H_2O$ per mL of the formulation;

about 0.45 to about 0.60 mg $NaH_2PO_4.2H_2O$ per mL of the formulation;

at least about 0.5 mg Polysorbate 20 per mL of the formulation; and water for injection as the solvent; wherein the amounts of $Na_2HPO_4.7H_2O$ and $NaH_2PO_4.2H_2O$ are adjusted to bring the pH of the formulation to about 7.4 to 7.6.

16. The formulation of claim 15, comprising about 1.0 to about 2.0 mg of said Polysorbate 20 per mL of the formulation.

17. A method of providing alpha interferon in a form and concentration able to be systemically delivered to a patient via the lungs, said method comprising the steps of:

providing an aqueous alpha interferon solution having a known, selected alpha interferon biological activity, and containing a buffering system and a stabilizing agent; and aerosolizing the solution to form an aerosol of aqueous droplets, wherein the aerosol has a fine particle fraction of at least about 50 percent, and wherein the aqueous solution comprise about 4.0 to about 12.0 mg alpha interferon per mL of the solution.

18. The method of claim 17, wherein the aerosol has a fine particle fraction of about 90 to 100 percent.

19. The method of claim 17, wherein said fine particle fraction comprises particles having an aerodynamic diameter of less than about 6.5 microns.

20. The method of claim 19, wherein said fine particle fraction comprises particles having an aerodynamic diameter of less than about 5 microns.

21. The method of claim 20, wherein said fine particle fraction comprises particles having an aerodynamic diameter of less than about 3.5 microns.

22. The method of claim 17, wherein the stabilizer comprises a high purity stabilizer.

23. The method of claim 17, wherein the stabilizing agent comprises a poly(oxy-1,2-ethanediyl)derivative.

24. The method of claim 23, wherein the poly(oxy-1,2-ethanediyl) derivative comprises sorbitan, monododecanoate.

25. The method of claim 17, wherein the stabilizing agent comprises Polysorbate 20 in an amount of at least about 0.5 mg per mL of the solution.

26. The method of claim 25, wherein the Polysorbate 20 is in an amount of at about 1.0 to about 2.0 mg per mL of the solution.

27. The method of claim 23, wherein the poly(oxy-1,2-ethanediyl) derivative comprises a high purity poly(oxy-1,2-ethanediyl) derivative.

28. The method of claim 17, wherein the buffering system comprises $Na_2HPO_4.7H_2O$ and $NaH_2PO_4.2H_2O$, in amounts which are adjusted to make the pH of the solution about 7.4 to about 7.6.

29. A method of administering alpha interferon to the deep lung of a patient in a form and concentration able to be systemically absorbed to provide a therapeutic dose, said method comprising the steps of:

providing an aqueous alpha interferon solution being free of human blood-derived products and animal blood-derived products and comprising about 4.0 to about 12.0 mg alpha interferon per mL; a buffer system capable of maintaining the pH of the solution within the range of about 7.0 to 8.0; a poly(oxy-1,2-ethanediyl) derivative; and water;

aerosolizing the solution to form an aerosol of aqueous droplets, wherein the aerosol has a fine particle fraction of at least about 50 percent; and delivering the aqueous droplets to the patient's respiratory tract.

30. The method of claim 29, wherein said fine particle fraction is about 90 to about 100%.

31. The method of claim 29, wherein said fine particle fraction comprises particles having an aerodynamic diameter of less than about 6.5 microns.

32. The method of claim 31, wherein said fine particle fraction comprises particles having an aerodynamic diameter of less than about 5 microns.

33. The method of claim 32, wherein said fine particle fraction comprises particles having an aerodynamic diameter of less than about 3.5 microns.

34. The method of claim 17, wherein the stabilizing agent comprises high purity Polysorbate 20.

* * * * *